United States Patent [19]
Pierce et al.

[11] Patent Number: 5,005,401
[45] Date of Patent: Apr. 9, 1991

[54] NONCONTACT ON-LINE MEASUREMENT OF THE VISCOSITY OF LIQUID PAINT

[75] Inventors: Brian M. Pierce, Moreno Valley; David B. Chang, Tustin, both of Calif.

[73] Assignee: Hughes Aircraft Company, Los Angeles, Calif.

[21] Appl. No.: 478,893

[22] Filed: Feb. 12, 1990

[51] Int. Cl.$^5$ .................... G01N 11/00; G01N 13/02
[52] U.S. Cl. ......................................... 73/54; 73/64.4
[58] Field of Search .................................. 73/54, 64.4

[56] References Cited

U.S. PATENT DOCUMENTS

| | | | |
|---|---|---|---|
| 2,966,058 | 12/1960 | McSkimin | 73/54 X |
| 4,512,183 | 4/1985 | Alexander | 73/64.4 |
| 4,691,714 | 9/1987 | Wong et al. | 73/54 X |

FOREIGN PATENT DOCUMENTS

| | | | |
|---|---|---|---|
| 1124201 | 11/1984 | U.S.S.R. | 73/64.4 |
| 1260753 | 9/1986 | U.S.S.R. | 73/54 |
| 1283621 | 1/1987 | U.S.S.R. | 73/64.4 |

Primary Examiner—Hezron E. Williams
Assistant Examiner—Joseph W. Roskos
Attorney, Agent, or Firm—Michael W. Sales; Wanda Denson-Low

[57] ABSTRACT

A method and apparatus for non-contact measurement of the viscosity of a liquid such as paint. In accordance with the method and apparatus, the surface of a liquid is perturbed with a standing wave of predetermined wavelength. This perturbation is effected by directing a burst of air against the surface of the liquid using periodically spaced air nozzles. The frequency and rate of decay of the induced surface wave is measured using typically optical means including a reflected light beam. The measured frequency and decay rate are combined with the known depth of the liquid sample in a computing circuit to provide a measurement of fluid viscosity.

19 Claims, 2 Drawing Sheets

NONCONTACT ON-LINE MEASUREMENT OF THE VISCOSITY OF LIQUID PAINT

BACKGROUND

The present invention relates to a method and apparatus for measuring the viscosity of fluids, and more particularly, to a noncontact method of measuring frequency and decay of induced oscillation in a fluid surface. The sprayability of paint is largely determined by surface tension ($\sigma$) and viscosity ($\eta$). On-line monitoring of $\sigma$ and $\eta$ is important because these properties fluctuate over time. If these fluctuations are ignored, a less than optimal application of the paint is achieved.

Presently, liquid paint viscosity in most industrial plants is determined manually at the beginning of each working day by collecting samples of paint and measuring the time it takes for the samples to flow through a calibrated orifice or a constriction in a tube. However, this method does not easily lend itself to automated, on-line, noncontact monitoring of $\sigma$ and $\eta$. Other conventional methods employed to measure the viscosity of fluids also require contact with the fluid. Such methods include the falling-sphere method, capillary tube method, rotating cylinder method, and disk method, as well as ultrasonic wave velocity and attenuation methods.

It is possible to determine the viscosity of a fluid in a noncontact manner by measuring the Brillouin scattering of laser light. The line widths of Brillouin-scattered light are directly related to the viscosity of the fluid. The disadvantage of using Brillouin scattering for measuring the viscosity of paint is the opacity of paint to light, and the corresponding high intensities of laser light required to observe Brillouin scattering.

Accordingly, there exists a need for a rapid, on-line, noncontact method that measures the viscosity of a liquid, such as paint. It is also desirable to measure the surface tension of the fluid, because for certain paints, for example, there is also a high correlation between paint sprayability and surface tension. It is therefore desirable to have a non-contact method of measuring paint viscosity to obviate clogging of test components to reduce maintenance costs.

SUMMARY OF THE INVENTION

Broadly, one method in accordance with the present invention comprises the following steps. An array of periodically spaced nozzles is suspended above and directed substantially normal to the surface of a sample of a liquid, such as paint, having a known depth. A burst of air is forced through the nozzles to produce a surface wave in the liquid having a wavelength equal to the periodic spacing of the array of nozzles. A light beam is reflected from the surface of the liquid and is optically detected to measure the damping of the surface wave and the surface wave frequency. This damping ($\gamma$) and frequency ($\omega$) is then used to determine the two unknowns, $\eta$ and $\sigma$. The mathematical analysis that establishes the relationship between $\gamma$, $\omega$, $\eta$ and $\sigma$ is provided in the Appendix hereto.

In one specific embodiment, a light beam is reflected off the surface of the liquid and the movement of the reflected light beam is measured to determine the motion of the surface wave. In another specific embodiment, a low-power laser is used as the light source. The laser beam is directed normal to the surface of the liquid, and changes in the height of the liquid induced by the surface wave are detected by interferometry measurement methods.

In yet another specific embodiment of the invention, a burst of compressed air is issued through a second array of nozzles having a different periodic spacing than the first array and at the same pressure as that of the first burst. The second burst excites a surface wave with a different wavelength than in the first burst. The periodic spacing of the second array is different from that of the first array. The damping and frequency of the induced surface wave is optically measured to provide a second independent set of data, from which $\sigma$ and $\eta$ can be derived. The values of $\sigma$ and $\eta$ determined from the two sets of $\gamma$ and $\omega$ measurements may be averaged for increased accuracy.

In still another embodiment, bursts of compressed air are directed through the two arrays of nozzles at pressures different from that of the measurements in the above sequence and the wavelength and damping and frequency are remeasured. Because liquid paints are thixotropic, non-Newtonian liquids, their viscosities are a function of the force or pressure applied to them, and is a function of shear forces within the fluid. Thus, the additional sets of measurements assist in defining the functional relationship between liquid paint viscosity and applied pressure.

Apparatus in accordance with the principles of the present invention provides a means for measuring the viscosity of a liquid. The apparatus comprises means for initiating a surface wave of predetermined wavelength on a fluid sample of known depth. An optical device is adapted to direct a beam of light at the surface of the liquid at a critical angle of reflection, and a photodetector, for example, is positioned to detect the presence of the beam when the liquid is at rest. The periodic interruption of the beam by surface waves when the liquid is set in motion produces a frequency signal indicative of the frequency of oscillation of the liquid. The frequency pulses are combined with information indicating that the motion of wave has ceased, in order to measure the decay rate of the surface wave. A computing circuit is connected to receive these signals and determine the viscosity of the fluid as a function of wavelength, frequency, decay rate and the depth of fluid sample.

In a specific embodiment of the invention, the apparatus for initiating the surface wave includes a plurality of air nozzles arranged in a periodic array with the periodic spacing of the nozzles determining the wavelength of the surface wave. In yet another specific embodiment of the invention, a plurality of arrays of nozzles are sequentially used to produce surface waves of predetermined different wavelengths and the measurements determined therefrom are averaged by the computing circuit.

It is therefore an advantage of the invention to provide an improved method for measuring viscosity of a liquid. It is another advantage of the invention to provide such a method and apparatus which can measure the viscosity of an opaque liquid without contacting the liquid. Yet another advantage of the invention is to provide a viscosity measuring method and apparatus for effecting measurements quickly and easily without contacting the liquid thus enabling on-line measurement of fluid viscosity. Still another advantage of the invention is to provide a viscosity measuring method and apparatus in which enables measurement of fluid surface tension. Another advantage of the invention is to provide a viscosity measuring method and apparatus in which a surface wave of known wavelength is induced in the surface of an opaque liquid by means such as a periodic array of air jets, and the frequency and decay rate of the surface wave are detected by employing a beam of light and photodetector.

BRIEF DESCRIPTION OF THE DRAWINGS

The various features and advantages of the present invention may be more readily understood with reference to the following detailed description taken in conjunction with the accompanying drawings, wherein like reference numerals designate like structural elements, and in which.

DETAILED DESCRIPTION

Figure 1:
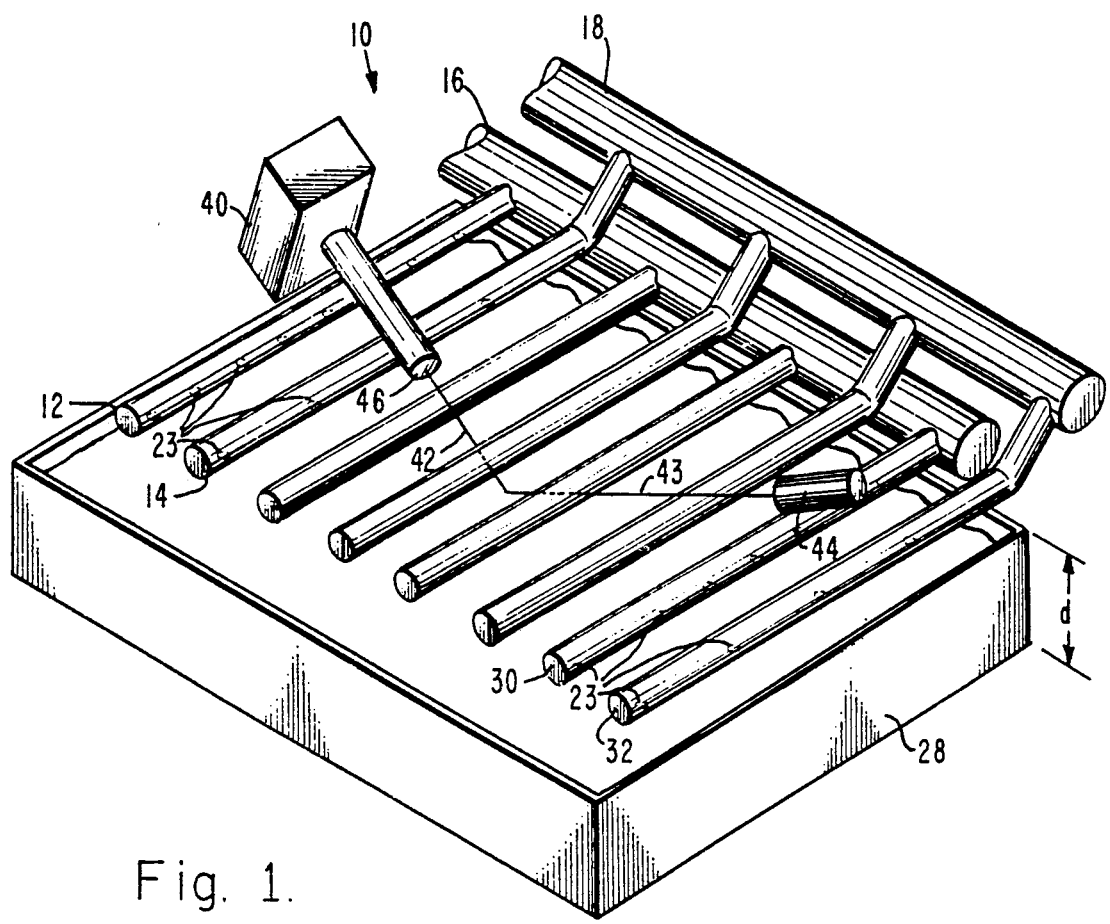
FIG. 1 is a perspective drawing of an apparatus in accordance with the principles of the present invention.
Figure 2:
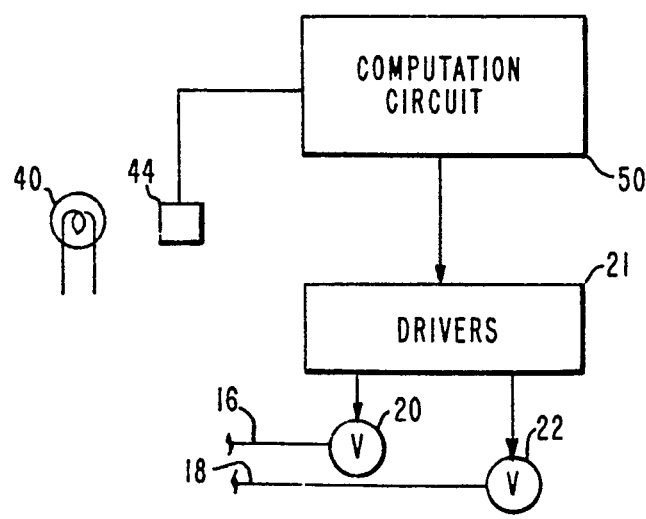
FIG. 2 is an illustration showing a control and computation circuit for use with the apparatus of FIG. 1.

Referring now to FIGS. 1 and 2 of the drawings, FIG. 1 illustrates one embodiment of a viscosity measuring apparatus 10 in accordance with the principles of the present invention, while FIG. 2 illustrates a control and computation circuit 50 for use with the apparatus 10 of FIG. 1. The apparatus 10 includes a plurality of air nozzles comprising first and second air nozzle arrays 12, 14 that respectively communicate with separate air manifolds 16, 18. The manifolds 16, 18 are pneumatically connected through electrically operated solenoid valves 20, 22 controlled by a driver circuit 21 shown in FIG. 2 to a source of pressurized air (not shown in the drawings). The nozzle arrays 12, 14 are provided with a plurality of spaced nozzles 23. The peridicity of the nozzle arrays 12 of the second air manifold 18 is different from the periodicity of the nozzle arrays 14 of the first air manifold 16. The nozzles 23 are positioned in spaced relationship above a surface 24 of a sample of a liquid 26, such as paint. The liquid 26 is contained within a sample pan 28, and the depth (d) of the liquid 26 is set at a known dimension, fixed by the depth of the pan 28, or by filling the pan 28 to a predetermined depth mark, or the like.

A light source 40 and a detector, such as a photodetector 44, are arranged above the surface 24 in order to produce a beam of light that is made incident upon the surface 24, is reflected therefrom, and is detected subsequent to its reflection from the surface 24. The photodetector 44 is monitored by a computation circuit 50 shown in FIG. 2, which also controls the activation of the air manifolds 16, 18.

Figure 4:
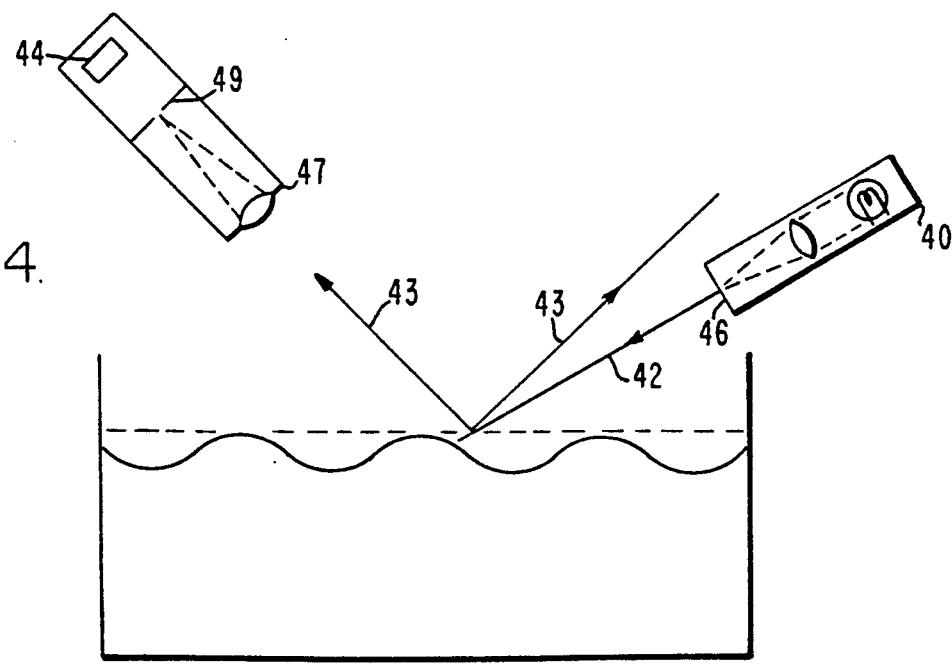
FIG. 4 is an illustration showing an arrangement of optical components for measuring the frequency and decay rate of a surface wave in the apparatus of FIG. 1.

Various optical arrangements may be provided to produce any desired reflected beam 43. For example, the light source 40 may produce a very bright light image at an orifice 46 as shown in FIG. 4. The detector may comprise the photodetector 44 that may be provided with a lens 47 that focuses an image of the orifice 46 onto a mask aperture 49 positioned in front of the photodetector 44, as is shown in FIG. 4.

In operation, the light source 40 produces a highly focused light beam 42 that is directed between the nozzle arrays 12, 14 at an angle such that beam 42 is reflected from the surface 24 (reflected beam 43) when it is motionless, and illuminates the photodetector 44. To accomplish this, the reflected beam 43 is reflected between different ones of the nozzle arrays 30, 32 where it is subsequently detected by the photodetector 44.

Figure 3:
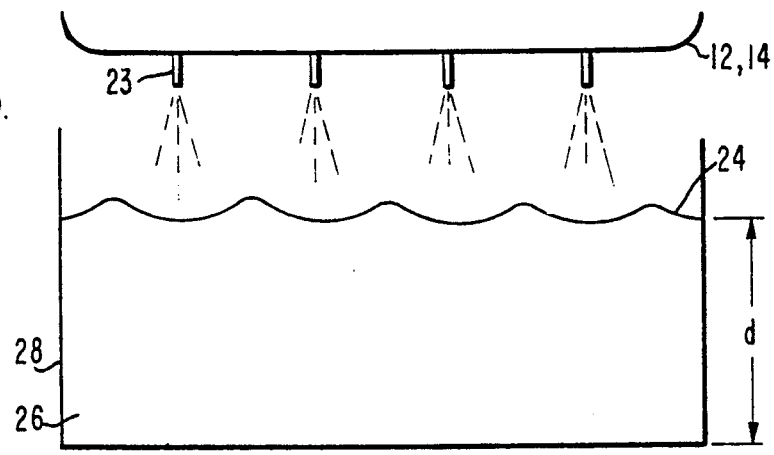
FIG. 3 is an illustration showing the production of a surface wave of predetermined wavelength by a plurality of air nozzles employed in the apparatus of FIG. 1.

Any disturbance in the surface 24 of the liquid 26, as shown in FIG. 3, for example, such as by bursts of air from the nozzles 23, will cause movement of the image of the orifice 46. If this movement is periodic, the image will synchronously move into and out of the image field of the photodetector 44. This produces a pulsed output from the photodetector 44. This pulsed output will have a frequency equal to the frequency of oscillation or periodic movement of the surface 24.

The mathematical expression for the surface wave in the liquid 26 is given by the relationship $A(x, t) = a_0 e^{-\gamma t} e^{i(kx+\omega t)}$, where k is equal to $2\pi/\lambda$, $\omega$ is the angular frequency, $a_0$ is the initial wave amplitude at $t=0$, and $\gamma$ is the damping coefficient of the liquid 26. The damping coefficient can be expressed as a function of surface tension ($\sigma$) and viscosity ($\eta$) of the liquid 26, and is given by the equation $$\gamma = a_0 e^{-\gamma t} e^{L(\nu x + \omega t)} * (d^3/\lambda^4) * (\sigma/\eta),$$

where $\gamma$ is the damping coefficient associated with the liquid, d is the sample depth, $\lambda$ is the wavelength of the surface wave in the liquid 26. A more detailed mathematical analysis relating $\gamma$, $\omega$, $\eta$ and $\sigma$ is given in the Appendix hereof.

From this analysis it is apparent that viscosity is a function of the wavelength of a standing wave, the frequency of oscillation of the wave, and the damping coefficient of the oscillations. This relationship does not apply under all conditions, such as when shear forces in the liquid are at high levels, for example. However, this relationship is highly accurate under conditions of relatively low shear forces, frequencies, and wave magnitudes.

In summary, then, the viscosity measuring apparatus 10 in accordance with the principles of the present invention provides a means for measuring the viscosity of a liquid 26. The apparatus 10 comprises means for initiating a surface wave of predetermined wavelength in the liquid 26. The means for initiating a surface wave includes the plurality of air nozzles 23 arranged in a periodic array with the periodic spacing of the nozzles 23 determining the wavelength of the surface wave. The light source 40 is adapted to direct the beam of light 42 at the surface 24 of the liquid 26 at a critical angle of reflection, and the photodetector 44 is positioned to detect the presence of the reflected beam 43. The periodic interruption of the beam 43 by surface waves when the liquid 26 is set in motion produces a frequency signal indicative of the frequency of oscillation of the liquid 26. The frequency pulses are combined with information indicating that motion of the wave has ceased, in order to measure the decay rate of the surface wave. The computation circuit 50 is connected to receive these signals and determine the viscosity of the liquid as a function of wavelength, frequency, decay rate and the depth of the liquid 26. In addition, a plurality of arrays of nozzles 23 may be sequentially employed to produce surface waves of predetermined different wavelengths and the measurements determined therefrom are averaged by the computation circuit 50.

The present invention also comprises a plurality of methods of determining the viscosity of a liquid 26. One such method comprises the following steps. An array of periodically spaced nozzles 23 is suspended above and directed substantially normal to the surface 24 of a sample of a liquid 26, such as paint, having a known depth. A burst of air is forced through the nozzles 23 to produce a surface wave in the liquid 26 having a wavelength equal to the periodic spacing of the array of nozzles 23. A light beam 42 provided by a light source 40 is reflected from the surface 24 of the liquid 26 and is optically detected to measure the damping of the surface wave and the surface wave frequency. A low-power laser may be used as the light source 40. The laser beam is directed normal to the surface 24 of the liquid 26, and changes in the height of the liquid 26 induced by the surface wave are detected by interferometry measurement methods.

A burst of compressed air may also issued through a second array of nozzles 23 having a different periodic spacing than the first array and at the same pressure as that of the first burst. The second burst excites a surface wave with a different wavelength than in the first burst. The damping and frequency of the induced surface wave is measured to provide two independent sets of data. The two sets of data may then be averaged for increased accuracy. Furthermore, bursts of compressed air may directed through the two arrays of nozzles at pressures different from that of the measurements in the above sequence and the wavelength and damping and frequency are remeasured. Because liquid paints, for example, are thixotropic, non-Newtonian liquids, their viscosities are a function of the force or pressure applied to them, and is a function of shear forces within the fluid. Thus, the additional sets of measurements assist in defining the functional relationship between liquid paint viscosity and applied pressure.

More specifically, a sample of the liquid 26, such as paint, that is to be tested, is deposited in the sample pan 28. This operation may be performed in a manual or automatic fashion. The nozzle arrays 12, 14 are positioned above the pan 28 with the nozzle arrays 12, 14 directed substantially normal to the surface 24. The horizontal spacing between the nozzle arrays 12, 14 is periodic. When both nozzle arrays 12, 14 are simultaneously energized by momentary energization of solenoid valves 20, 22, the periodic spacing between the arrays 12, 14 will be half of the periodic spacing when only one nozzle array 12 is energized.

Initially, a burst of compressed air at a given known pressure is issued through one of the nozzle arrays 12, 14 and against the surface 24 of the liquid 26. In response to this pertubation, a surface wave is excited, the surface wave having a wavelength (1) equal to the spacing of the first set of nozzle arrays 12.

The damping of the surface wave and its frequency may be optically detected in a noncontact manner using the apparatus 10 of FIG. 1. This measurement simply involves the noncontact detection of the intensity of the light beam 43 reflected from the surface 24 of the liquid 26. This reflection is in response to the motion of the surface wave. Alternatively, the frequency and damping may be measured with a low power laser as the light source 40. The laser beam is directed normal to the surface 24 of the liquid 26 and changes in the height of liquid 26 induced by this surface wave are detected.

Once the optical detection system has determined that the surface of the liquid 26 is calm, a second burst of compressed air is issued through both nozzle arrays 12, 14 at the same pressure as that of the first burst. The second burst excites a surface wave with a different wavelength than that generated by the first burst, thus providing two independent sets of data in order to generate average values of viscosity. This data, (frequency, and time lapse for decay) of the wave is provided to the computation circuit 50. Typically, the computation circuit 50 includes a timing circuit as well as a pulse detector. The computation circuit 50 registers both the existence of the wave and the time lapse period from initiation to the time when the wave has decayed sufficiently to be no longer detectable. Counting of the number of cycles during the time lapse period provides the necessary data for the computations. The steps of the method may be repeated at a sufficient number of known pressures to generate additional data for data averaging.

From the above description it should now be apparent that the present invention provides both a method and an apparatus that provides for noncontact measurement of the viscosity of a liquid. The method and apparatus is particularly adapatable to applications such as measurement of the viscosity of liquid paint. The accurate determination of the paint viscosity is of significant importance in providing uniform painting on surfaces such as automobile bodies. Since the method is a noncontact method, contamination of the equipment is minimized. The taking of samples may be effected automatically and continuously throughout a working day, thereby assuring long term paint uniformity. It will also be observed that in accordance with the method and apparatus of the present invention, it is possible to measure not only the viscosity of the liquid, but also its surface tension. Surface tension is also an important indicator of proper paint consistency.

Thus there has been described a new improved method and apparatus for noncontact measurement of liquid viscosity. It is to be understood that the above-described embodiments are merely illustrate of some of the many specific embodiments which represent applications of the principles of the present invention. Clearly, numerous and other arrangements can be readily devised by those skilled in the art without departing from the scope of the invention.

APPENDIX

The following derivation contemplates exciting "surface waves," i.e., disturbances of the liquid having the mathematical form $$e^{+\gamma y} e^{ikx} e^{i\omega t} \text{ for } y<0 \tag{1}$$

The equations describing the liquid are the standard Navier-Stokes equations. Thus, the specific Non-Newtonian character of the liquid are ignored. However, for paint, which is thixotropic, the non-Newtonian behavior can be approximated by choosing the appropriate viscosity $\eta$ for any flow rate of interest. The basic equations are:

$$\text{CONTINUITY: } \nabla \cdot v_1 = -i\omega \left( \frac{\rho_1}{\rho_0} \right) \tag{2}$$

$$\text{MOMENTUM: } i\omega v_1 = \rho_1 g - \frac{1}{\rho_0} \nabla \cdot P_1 \tag{3}$$

-continued $$P_{1ij} = \delta_{ij}P_1 - \eta\left[\left(\frac{\partial v_{1i}}{\partial x_j} + \frac{\partial v_{1j}}{\partial x_i}\right) - \frac{2}{3}\delta_{ij} \cdot v_1\right] \quad (4)$$

PRESSURE: $P_1 = c_s^2 \rho_1$ (5)

Here $v_1$ denotes the perturbed velocity, $\rho_1$ and $\rho_0$ are the perturbed and equilibrium density, $g = -i_y$ is the acceleration of gravity, $P_1$ is the perturbed fluid pressure, $C_s$ is the speed of sound, $\eta$ is the viscosity and $x_i$ ($i=1, 2, 3$) denote the Cartesian coordinates.

For disturbances of the form given by equation (1):

$$\frac{\partial}{\partial x} \to ik; \frac{\partial}{\partial y} \to \gamma \text{ and } \frac{\partial}{\partial z} \to 0 \quad (6)$$

Accordingly, $$\nabla \cdot v_1 = ikv_{1x} + \gamma v_{1y} \quad (7)$$

$$\rho_1 = \frac{\rho_0}{i\omega}[ikv_{1x} + \gamma v_{1y}] \quad (8)$$

$$i\omega v_{1x} = -\frac{ik}{\rho_0}\{P_{1xx} + P_{1xy} + P_{1xz}\} \quad (9)$$

$$i\omega v_{1y} = -\rho_1 g - \frac{\gamma}{\rho_0}\{P_{1yx} + P_{1yy} + P_{1yz}\} \quad (10)$$

$$i\omega v_{1z} = 0 \quad (11)$$

and the pressure tensor is given by $$P_{1xx} = P_1 - \eta[2ikv_{1x} - \tfrac{2}{3}(ikv_{1x} + \gamma v_{1y})] \quad (12)$$

$$P_{1yy} = P_1 - \eta[2\gamma v_{1y} - \tfrac{2}{3}(ikv_{1x} + \gamma v_{1y})] \quad (13)$$

$$P_{1xy} = P_{1yx} = -\eta[ikv_{1y} + \gamma v_{1x}] \quad (14)$$

$$P_{1xz} = P_{1yz} = 0 \quad (15)$$

At $y=0$, the surface tension and gravity forces require that $$P_{1yy} + P_{1yx} = \rho_0 g y_1 (y=0) + \Gamma k^2 y_1 (y=0) \quad (16)$$

where $$y_1 (y=0) = \frac{1}{i\omega} v_{1y}(y=0) \quad (17)$$

Algebraic manipulation of equations (2)–(17) gives the dispersion relation for surface waves. Equations (5) and (8) give $$P_1 = -c_s^2 \frac{\rho_0}{i\omega}[ikv_{1x} + \gamma v_{1y}] \quad (18)$$

Substitution of equations (12), (14), and (18) into equation (9) yields:

$$i\omega v_{1x} = -\frac{ik}{\rho_0}\left[-\frac{\rho_0 c_s^2}{i\omega}(ikv_{1x} + \gamma v_{1y}) - \right.$$

$$\left. \eta\left\{\frac{1}{3}ikv_{1x} - \frac{2}{3}\gamma v_{1y}\right\} - \eta ikv_{1y} - \eta\gamma v_{1x}\right] \quad (19)$$

Substitution of equations (8), (13), (14), and (18) into equation (10) yields:

$$i\omega v_{1y} = +\frac{\rho_0 g}{i\omega}[ikv_{1x} + \gamma v_{1y}] - \frac{\gamma}{\rho_0}\left[-\eta(ikv_{1y} + \gamma v_{1x}) - \right.$$

$$\left. \frac{c_s^2 \rho_0}{i\omega}(ikv_{1x} + \gamma v_{1y}) - \eta\left\{\frac{4}{3}\gamma v_{1y} - \frac{2}{3}ikv_{1x}\right\}\right] \quad (20)$$

Equations (19) and (20) determine $\gamma(\omega,k)$:

$$\left(-i\omega + \frac{ik}{\rho_0}\frac{\rho_0 c_s^2}{i\omega}ik + \frac{ik}{\rho_0}\eta\frac{4}{3}ik + \eta\gamma\frac{ik}{\rho_0}\right)v_{1x} + $$

$$\left(\frac{ik}{\rho_0}\frac{\rho_0 c_s^2}{i\omega}\gamma - \frac{ik}{\rho_0}\eta\frac{2}{3}\gamma + \frac{ik}{\rho_0}\eta ik\right)v_{1y} = 0 \quad (21)$$

$$\left(\frac{\rho_0 gik}{i\omega} + \frac{\gamma}{\rho_0}\eta\gamma + \frac{\gamma}{\rho_0}\frac{c_s^2 \rho_0}{i\omega}ik - \frac{\gamma}{\rho_0}\eta\frac{2}{3}ik\right)v_{1x} + $$

$$\left(-i\omega + \frac{\rho_0 g\gamma}{i\omega} + \frac{\gamma\eta}{\rho_0}ik + \frac{\gamma}{\rho_0}\frac{c_s^2\rho_0\gamma}{i\omega} + \right.$$

$$\left. \frac{\gamma}{\rho_0}\eta\frac{4}{3}\gamma\right)v_{1y} = 0 \quad (22)$$

Thus:

$$\left(-i\omega - \frac{k^2 c_s^2}{i\omega} - \frac{4}{3}\frac{\eta k^2}{\rho_0} + \frac{i\gamma\eta k}{\rho_0}\right)\left(-i\omega + \frac{\rho_0 g\gamma}{i\omega} + \right. \quad (23)$$

$$\left. \frac{i\gamma\eta k}{\rho_0} + \frac{\gamma^2 c_s^2}{i\omega} + \frac{\eta\gamma^2 4}{\rho_0 3}\right) - \left(\frac{\rho_0 gk}{\omega} + \frac{\gamma^2\eta}{\rho_0} + \frac{\gamma c_s^2 k}{\omega} - \right.$$

$$\left. \frac{i\gamma\eta k2}{3\rho_0}\right)\left(\frac{kc_s^2\gamma}{\omega} - \frac{i\gamma\eta k2}{3\rho_0} - \frac{k^2\eta}{\rho_0}\right) = 0$$

can be solved for $\gamma$. When $\eta = 0$, equation (23) becomes:

$$\left(-i\omega - \frac{k^2 c_s^2}{i\omega}\right)\left(-i\omega + \frac{\rho_0 g\gamma}{i\omega} + \frac{\gamma^2 c_s^2}{i\omega}\right) - \quad (23a)$$

$$\left(\frac{\rho_0 gk}{\omega} + \frac{\gamma c_s^2 k}{\omega}\right)\left(\frac{kc_s^2\gamma}{\omega}\right) = 0$$

Ignoring the gravity term as small, equation (23a) further simplifies to:

$$\gamma^2 = k^2 - \frac{\omega^2}{c_s^2} \quad (23b)$$

and $\gamma \to k$ at low frequencies.

The boundary condition (equation (16)) is written:

$$-\eta(ikv_{1y} + \gamma v_{1x}) - \frac{c_s^2\rho_0}{i\omega}(ikv_{1x} + \gamma v_{1y}) - \quad (24)$$

-continued $$\eta\left(\frac{4}{3}\gamma v_{1y} - \frac{2}{3}ikv_{1x}\right) = (\rho_0 g + \Gamma k^2)\frac{v_{1y}}{i\omega}$$

where the vlx and vly are evaluated at y=0. Thus, $$\left[\frac{1}{i\omega}(\rho_0 g + \Gamma k^2) + \eta ik + \frac{\rho_0 c_s^2 \gamma}{i\omega} + \frac{\eta 4\gamma}{3}\right]\frac{v_{1y}}{v_{1x}} = \tag{25}$$

$$\left(-\eta\gamma - \rho_0 c_s^2 \frac{k}{\omega} + \frac{2}{3}\eta ik\right)$$

Again, if the viscosity terms are ignored, and low frequencies are considered, then $$\frac{v_{1y}}{v_{1x}} \approx -\frac{i\gamma}{k} \tag{26}$$

and equation (25) becomes approximately $$\left[\frac{1}{i\omega}(\rho_0 g + \Gamma k^2) + \frac{\rho_0 c_s^2 \gamma}{i\omega}\right]\left[-\frac{i\gamma}{\omega}\right] = -\rho_0 c_s^2 \frac{k}{\omega} \tag{27}$$

If equation (23b) is then used, $$\omega^2 \approx \left(g + \frac{\Gamma k^2}{\rho_0}\right)\gamma, \tag{28}$$

and for low frequencies, $$\omega^2 \approx gk + \frac{\Gamma k^3}{\rho_0} \tag{29}$$

Equation (29) gives the usual gravity wave $$\omega^2 \approx gk \ (k \to 0) \tag{30}$$

at long wavelengths, and the usual surface tension wave $$\omega^2 \approx \frac{\Gamma k^3}{\rho_0} \ (\text{large } k) \tag{31}$$

at short wavelengths.

The effect of viscosity $\eta$ is to cause damping of the surface waves and to cause a slight shift in the frequency of oscillation for a given wavelength ($2\pi/k$). The exact dispersion relation describing these effects can be obtained from equations (23), (25), and (21).

The foregoing suggests that both the surface tension and viscosity of a liquid can be determined by exciting a surface oscillation of some wavelength at the air-liquid interface, and observing both the frequency of oscillation and damping of the surface wave. A check is provided by exciting at more than one wavelength.

What is claimed is:

1. Apparatus for measuring the measuring the viscosity of a liquid, comprising:
    means for initiating a surface wave of predetermined wavelength in a fluid sample of known depth;
    frequency signal generating means for generating a frequency signal as a function of the surface wave frequency;
    decay signal generating means for generating a decay signal as a function of the rate of decay of the surface wave magnitude; and
    computing circuit means connected to received the frequency and decay signals for computing the viscosity of the fluid as a function thereof.

2. The apparatus of claim 1 wherein the surface wave initiating means includes pneumatic means for directing a burst of air against the surface of the liquid.

3. The apparatus of claim 2 wherein the pneumatic means includes an array of air nozzles arranged in periodic spaced relationship, the spacing of the nozzles being the wavelength of the surface wave.

4. The apparatus of claim 3 wherein the frequency signal generating means includes light source means for reflecting a beam of light from the surface of the fluid when the liquid is still and photodetector means for detecting the reflected light beam, the surface wave causing the reflected beam to be reflected away from the photodetector means.

5. The apparatus of claim 4 wherein there are two arrays of air nozzles, the two arrays having different periodicity, and further including means for sequentially initiating the surface wave with the arrays to initiate two sequentially occurring surface waves of different wavelengths, the frequency signal generating means and the decay signal generating means generating a frequency signal and a decay signal in response to each of the sequentially occurring surface waves, the computing means computing the viscosity as an average of the computed viscosity computed as a function of the frequency and rate of decay of the two surface waves.

6. The apparatus of claim 5 wherein the computing circuit computes the viscosity in accordance with the relationship: $a_o e^{-\gamma t} e^{i(kx+\omega t)}$, where k is equal to $2\pi/\lambda$, $\omega$ is the angular frequency, $a_0$ is the initial wave amplitude at t=0, and $\gamma$ is the damping coefficient of the liquid.

7. The apparatus of claim 6 wherein the computing means further includes means for computing the surface tension of the fluid.

8. The apparatus of claim 7 wherein the liquid is an opaque liquid.

9. The apparatus of claim 8 wherein the liquid is paint.

10. The apparatus of claim 7 wherein the liquid is a thixotropic liquid.

11. A method of measuring the viscosity of a fluid comprising the steps of:
    (a) producing a surface wave of predetermined wavelength of the surface of a sample of liquid of known depth;
    (b) measuring the frequency of the surface wave;
    (c) measuring the rate of decay of the surface wave; and
    (d) computing the viscosity of the fluid as a function of the frequency of oscillation and rate of decay.

12. The method of claim 11 further including the step of sequentially producing a plurality of surface waves, each of a different wavelength and repeating steps b and, c and d, for each wavelength.

13. The method of claim 12 including preforming the wave producing step by directing a blast of air against the surface of the liquid from a plurality of periodically spaced air nozzles positioned above the surface of the fluid.

14. The method of claim 13 wherein the frequency and rate of decay measuring steps include reflecting a beam of light off the surface of the liquid, detecting the reflected beam, and measuring the time between detection of the light beam.

15. The method of claim 14 wherein the rate of decay measuring step includes measuring the time from initiation of the surface wave to the time oscillations of the surface wave are undetectable and counting the number of wave oscillations there between.

16. The method of claims 13 further including the step of repeating steps a, b, c, and d at a plurality of different pressures.

17. The method of claim 16 further including the step of computing the surface tension of the liquid as a function of the surface wave oscillation frequency and the rate of decay thereof.

18. The method of claim 16 wherein the liquid is an opaque liquid.

19. The method of claim 18 wherein the liquid is paint.

* * * * *